US006706675B1

(12) United States Patent
Demson et al.

(10) Patent No.: US 6,706,675 B1
(45) Date of Patent: Mar. 16, 2004

(54) TRANSLUCENT SOAP BAR COMPOSITION AND METHOD OF MAKING THE SAME

(75) Inventors: Robert Demson, Scottsdale, AZ (US); James Dalton, Scottsdale, AZ (US)

(73) Assignee: The Dial Corporation, Scottsdale, AZ (US)

(*) Notice: Subject to any disclaimer, the term of this patent is extended or adjusted under 35 U.S.C. 154(b) by 0 days.

(21) Appl. No.: 10/371,411

(22) Filed: Feb. 20, 2003

Related U.S. Application Data

(60) Provisional application No. 60/407,386, filed on Aug. 30, 2002.

(51) Int. Cl.[7] .................. A61K 7/50

(52) U.S. Cl. .................. 510/147; 510/141; 510/152; 510/153

(58) Field of Search .................. 510/141, 147, 510/152, 153

(56) References Cited

U.S. PATENT DOCUMENTS

| | | | |
|---|---|---|---|
| 3,729,421 | A | 4/1973 | Gibson et al. |
| 3,903,008 | A | 9/1975 | Deweever et al. |
| 3,926,828 | A | 12/1975 | O'Neill et al. |
| 4,206,069 | A | 6/1980 | Borrello |
| 4,285,826 | A | 8/1981 | Bertozzi et al. |
| 4,468,338 | A | 8/1984 | Lindberg |
| 4,493,786 | A | 1/1985 | Joshi |
| 4,564,462 | A | 1/1986 | Watanabe et al. |
| 4,582,626 | A | 4/1986 | Ferrara |
| 4,584,126 | A | 4/1986 | Joshi |
| 4,678,593 | A | 7/1987 | Ridley |
| 4,704,223 | A | 11/1987 | Gupta et al. |
| 4,714,563 | A | 12/1987 | Kajs et al. |
| 4,719,030 | A | 1/1988 | Williams et al. |
| 4,808,322 | A | 2/1989 | McLaughlin |
| 4,812,252 | A | 3/1989 | Nambudiry |
| 4,820,438 | A | 4/1989 | Zilch |
| 4,861,507 | A | 8/1989 | Gervasio |
| 4,865,757 | A | 9/1989 | Singh-Verma et al. |
| 4,976,953 | A | 12/1990 | Orr et al. |
| 4,980,078 | A | 12/1990 | Verite et al. |
| 5,041,234 | A | 8/1991 | Instone et al. |
| 5,196,131 | A | 3/1993 | Baumgartner et al. |
| 5,219,487 | A | 6/1993 | Heile, Jr. et al. |
| 5,225,098 | A | 7/1993 | Kacher et al. |
| 5,227,086 | A | 7/1993 | Kacher et al. |
| 5,246,614 | A | 9/1993 | Baumgartner et al. |
| 5,262,079 | A | 11/1993 | Kacher et al. |
| 5,264,144 | A | 11/1993 | Moroney et al. |
| 5,264,145 | A | 11/1993 | French et al. |
| 5,312,559 | A | 5/1994 | Kacher et al. |
| 5,340,492 | A | 8/1994 | Kacher et al. |
| 5,387,362 | A | 2/1995 | Tollens et al. |
| 5,417,876 | A | 5/1995 | Tokosh et al. |
| 5,417,878 | A | 5/1995 | Takahata et al. |
| 5,496,488 | A | 3/1996 | Kacher et al. |
| 5,540,852 | A | 7/1996 | Kefauver et al. |
| 5,540,853 | A | 7/1996 | Trinh et al. |
| 5,540,854 | A | 7/1996 | Fair et al. |
| 5,607,909 | A | 3/1997 | Kefauver et al. |
| 5,656,579 | A | 8/1997 | Chambers et al. |
| 5,703,026 | A | 12/1997 | Setser et al. |
| 5,705,462 | A | 1/1998 | Hormes et al. |
| 5,750,481 | A | 5/1998 | Del Vecchio et al. |
| 5,780,405 | A | 7/1998 | He et al. |
| 5,786,312 | A | 7/1998 | Post et al. |
| 5,795,852 | A | 8/1998 | He et al. |
| 5,856,283 | A | 1/1999 | Abbas et al. |
| 5,874,392 | A | 2/1999 | Halvorson et al. |
| 5,888,952 | A | 3/1999 | Subramanyam et al. |
| 5,895,780 | A | 4/1999 | Tokosh et al. |
| 5,898,027 | A | 4/1999 | Bardenberg et al. |
| 5,935,917 | A | 8/1999 | Farrell et al. |
| 5,952,276 | A | 9/1999 | de Ferran et al. |
| 5,952,289 | A | 9/1999 | Wise et al. |
| 5,962,382 | A | 10/1999 | Lambino |
| 5,972,859 | A | 10/1999 | Farrell et al. |
| 5,985,808 | A | 11/1999 | He et al. |
| 6,007,831 | A | 12/1999 | Fujiwara et al. |
| 6,143,704 | A | 11/2000 | Van Gunst et al. |
| 6,150,314 | A | 11/2000 | Clifton-White et al. |
| 6,156,714 | A | 12/2000 | Shimosato et al. |
| 6,162,775 | A | 12/2000 | Methmanus-Spaltro |
| 6,174,845 | B1 | 1/2001 | Rattinger et al. |
| 6,207,636 | B1 | 3/2001 | Benjamin et al. |
| 6,218,348 | B1 | 4/2001 | Aronson et al. |
| 6,242,398 | B1 | 6/2001 | Chambers et al. |
| 6,242,399 | B1 | 6/2001 | Chambers et al. |
| 6,255,265 | B1 | 7/2001 | Van Gunst et al. |
| 6,297,205 | B1 | 10/2001 | Saxena et al. |
| 6,310,015 | B1 | 10/2001 | Diez et al. |
| 6,326,339 | B1 | 12/2001 | Rattinger et al. |
| 6,342,470 | B1 | 1/2002 | Aronson et al. |
| 2001/0034311 | A1 * | 10/2001 | Saxena et al. .............. 510/152 |
| 2002/0045555 | A1 * | 4/2002 | Andreas et al. ............. 510/141 |
| 2003/0064901 | A1 * | 4/2003 | Diez et al. .................. 510/141 |

FOREIGN PATENT DOCUMENTS

WO WO 95/02035 1/1995

* cited by examiner

*Primary Examiner*—Necholus Ogden
(74) *Attorney, Agent, or Firm*—Snell & Wilmer LLP

(57) ABSTRACT

A soap bar composition includes a soap mixture, a polyalkylene glycol, at least one of glycerin and sorbitol, water; and optionally, free fatty acid. The soap bar composition exhibits translucent properties.

8 Claims, No Drawings

TRANSLUCENT SOAP BAR COMPOSITION AND METHOD OF MAKING THE SAME

CROSS-REFERENCE TO RELATED APPLICATION

This application claims priority to U.S. Provisional Patent Application, Ser. No. 60/407,386 entitled "Translucent Soap Bar Composition," filed on Aug. 30, 2002, which is incorporated by reference herein.

FIELD OF INVENTION

The present invention relates generally to soap compositions and their method of manufacture, and more particularly to soap compositions that exhibit translucent properties.

BACKGROUND OF THE INVENTION

Translucent soap bars are popular among consumers for their aesthetic appeal and their connotation of purity and high moisture content. Generally, a translucent bar soap is composed largely of one single homogeneous crystalline phase known as the "beta phase." The beta phase is one of four known crystalline phases of soap and imparts translucence, generally due to the small size of the soap crystals, which are too small to diffract light.

As used herein, the meaning of "translucent" is that which is generally employed and is generally in accordance with the usual dictionary definition. For example, a translucent soap is one that allows light to pass through it but the light may be so scattered, as by a small proportion of crystals or insolubles, such that it will not be possible to clearly identify objects behind the translucent soap. Furthermore, translucent soaps may include clear, colorless, and colored transparent soaps.

As with conventional, opaque soaps, it is popular to include additives, such as antibacterial agents, fragrance, vitamins and colorants, to translucent soaps bars to provide other beneficial characteristics. However, these additional ingredients may impair translucency of the final product. In such cases, it may be necessary during manufacturing to run the mix of ingredients through refining and milling processes multiple times before an acceptable translucency is achieved. Such additional processing increases manufacturing time, energy and manpower, thus increasing product costs and decreasing throughput.

Accordingly, there is a need for soap bar compositions that exhibit satisfactory translucency without undesirable processing. The present invention addresses this long felt, yet unresolved need.

SUMMARY OF THE INVENTION

This summary of the invention section is intended to introduce the reader to aspects of the invention. Particular aspects of the invention are pointed out in other sections herein below, and the invention is set forth in the appended claims which alone demarcate its scope.

In accordance with an exemplary embodiment of the present invention, a soap bar composition is provided. The soap bar composition includes a soap mixture, a polyalkylene glycol, at least one of glycerin and/or sorbitol, water, and optionally, free fatty acid. The soap bar composition exhibits translucent properties.

In accordance with a further exemplary embodiment of the present invention, a translucent soap bar is provided. The soap bar includes, by weight, about 65 to about 80% of a soap mixture, about 0.5 to about 5.0% of a polyethylene glycol having a molecular weight in the range of about 300 to about 800, about 4.5 to about 8.5% glycerin, about 12 to about 16% water, and, optionally, about 1.5 to about 3.0% of a free fatty acid.

In accordance with another exemplary embodiment of the present invention, a process for making soap bars is provided. The soap bars exhibit translucent properties and include a soap mixture, a polyethylene glycol having a molecular weight in the range of about 300–800, glycerin, water, and, optionally, a free fatty acid. The process includes saponifying oils with a caustic solution to form a soap mixture, optionally neutralizing unreacted caustic solution with the free fatty acid, and spray drying the soap mixture and ultimately forming soap pellets. Polyethylene glycol is added to the soap pellets to aid processing, and the mixture is then subjected to plodding, roll-milling and extrusion to form a soap ribbon. The soap ribbon is cut and stamped to form soap bars.

DETAILED DESCRIPTION

The following description is of exemplary embodiments only and is not intended to limit the scope, applicability or configuration of the invention in any way. Rather, the following description provides a convenient illustration for implementing various exemplary embodiments of the invention. Various changes to the described embodiments may be made without departing from the scope of the invention as set forth in the appended claims.

In one exemplary embodiment of the present invention, the translucent soap bar composition comprises a soap mixture. As used herein, the term "soap" is defined as any water-soluble salt of those fatty acids that contain about 8 or more carbon atoms. In an exemplary embodiment of the present invention, the soap mixture comprises at least one of sodium tallowate, sodium palmitate, sodium stearate and sodium palm kernelate, salts of fatty acids having alkyl chain lengths with 12 to 18 carbons. In a preferred embodiment of the invention, the soap mixture suitably comprises a blend of sodium tallowate, sodium palmitate, sodium stearate and sodium palm kernelate. It will be appreciated, however, that other fats and oils from which soaps may be produced can be employed, such as babassu oil, soybean oil, cottonseed oil, rapeseed oil or other comparable vegetable product, whale or fish oils and lards, and the like. Various other animal fats and oils may also be employed to produce soaps similar to tallow/palmitate/stearate/palm kernelate soaps mentioned above.

Generally, fatty acids with alkyl chains having 12 to 18 carbons are most desirable for soap production, as shorter alkyl chains may not produce the desired soap properties. Fatty acids with chain lengths having 20 carbons or more have very little solubility and may impede lathering.

In one embodiment of the translucent soap bar composition of the present invention, the soap mixture comprises about 65 to about 80% by weight of the translucent soap composition. In a preferred embodiment of the invention, the soap mixture comprises about 70 to about 75% by weight of the translucent soap composition. It will be appreciated, however, that any suitable amount of the soap mixture may be used to impart a cleaning benefit to the translucent soap bar. Generally, the soap mixture comprises more than about 60% by weight of the translucent soap composition, and more preferably more than about 70% by weight of the translucent soap composition.

In another exemplary embodiment of the present invention, sodium tallowate, sodium palmitate and sodium stearate comprises about 80 to about 90% by weight of the soap mixture and sodium palm kernelate comprises about 10 to about 20% by weight of the soap mixture. In a preferred embodiment, sodium tallowate, sodium palmitate and sodium stearate comprise on the order of about 85% of the soap mixture and sodium palm kernelate comprises on the order of about 15% of the soap mixture.

Preferably, the translucent soap composition of the present invention also comprises glycerin, sorbitol, or a mixture of glycerin and/or sorbitol. In one exemplary embodiment of the present invention, the translucent soap bar composition comprises about 4.5 to about 8.5% by weight glycerin. In a preferred embodiment, the translucent soap composition comprises about 6.0 to about 8.0% by weight glycerin.

Preferably, the transparent soap composition also comprises water. In one exemplary embodiment of the present invention, the transparent soap composition comprises about 10 to about 20% by weight water. In a preferred embodiment of the present invention, the transparent soap composition comprises about 12 to about 16% by weight water.

The translucent soap bar composition also comprises a polyalkylene glycol, which may include polyethylene glycols and polypropylene glycols, having a relatively low molecular weight. The inventors have found that use of a polyalkylene glycol having a relatively low molecular weight enhances the translucent properties of the soap bar composition of the present invention. In one embodiment of the invention, the translucent soap bar composition comprises polyethylene glycol having a molecular weight in the range of about 300 to about 800. In a preferred embodiment of the invention, the translucent soap bar composition comprises polyethylene glycol having a molecular weight of 400, which is typically sold commercially as "PEG-8". In another exemplary embodiment of the present invention, the translucent soap bar composition comprises about 0.5 to about 5.0% by weight polyethylene glycol. In a preferred embodiment of the invention, the translucent soap composition comprises about 1.0 to about 2.0% by weight polyalkylene glycol.

In another exemplary embodiment of the invention, the translucent soap bar composition may comprise free fatty acid. The free fatty acids generally may have alkyl chain lengths with 8 to 22 carbons, but preferably 12 to 18 carbons. An example of a suitable free fatty acid for use in the translucent soap composition of the present invention is lauric acid, although it will be appreciated that any suitable free fatty acid having an alkyl chain length of 8 to 22 carbon atoms may be used.

In another exemplary embodiment of the present invention, the translucent soap bar composition may comprise one or more other conventional processing aids and conventional additives, including organic and inorganic salts, chelating agents, vitamins, dyes, moisturizers, antibacterial agents, preservatives, antioxidants, conditioners, exfoliants, emollients, and the like.

A process for making translucent soap bars in accordance with one exemplary embodiment of the present invention will now be described. A soap mixture may be manufactured by saponifying suitable raw oils, such as, for example, tallow, palm oil, stearin oil and palm kernel oil, with a caustic solution, such as sodium hydroxide, to form a "neat soap." The pH of the neat soap may be alkaline when produced and can be suitably adjusted by the addition of an organic acid, such as citric acid. Free fatty acid may also be added to the neat soap to neutralize any undesirable excess caustic solution and to enhance the lather characteristics of the resulting soap. Optionally, at this stage of the process, preservative agents, chelating agents, and inorganic and/or organic salts may also be added. The neat soap may then be spray dried to reduce the moisture content of the soap, yielding soap pellets. In one embodiment of the invention, the water content is reduced to about 16 to about 19% by weight of the soap pellets.

Pre-mixes then may be formulated. The PEG-8 and colorants may be combined into a first pre-mix using, for example, a slurry tank agitator. Perfume and other active ingredients, such as an antibacterial agent, skin controlling agents, and other additives may be combined in the second pre-mix.

The soap pellets may then be transferred to an amalgamator where they are coated with the ingredients of the three pre-mixes. The three pre-mixes may be: added to the soap pellets sequentially or in unison. The coated pellets may then be double refined through a twin-screw formulation plodder and transported to a four-roll/double-pass mill and a first duplex plodder that pelletizes the soap. The refined formulated pellets may then be transported to the top hopper of a final duplex plodder at which point a recycle stream from a soap press, described below, is introduced. The mix may be combined through the top hopper, preferably with screens and compaction plates removed. A lower vacuum plodder then may extrude the soap into a ribbon that may be cut into slugs. The slugs may be stamped into finished bars using an automatic soap press, from which the recycle stream described above is produced.

While the above process describes one embodiment for manufacturing the translucent soap bar composition of the present invention, it will be appreciated that the translucent soap bar, composition of the present invention is not limited to the method of manufacture described above, but can be manufactured using any suitable process. For example, the soap may be manufactured in a batch process where all the ingredients are combined in situ and processed to refine the crystallinity of the mixture to produce a translucent soap bar composition. In another exemplary embodiment, the translucent soap composition may be subjected to additional plodding and/or milling to further enhance the translucency of the resulting composition.

An exemplary embodiment of the translucent soap bar composition of the present invention, with each of the components set forth in weight percent of the total soap bar composition, is as follows:

| Component | wt. % |
|---|---|
| soap (sodium tallowate, sodium palm kernelate, sodium palmitate and sodium stearate) | 72.0129 |
| water | 14.3700 |
| glycerin | 7.6060 |
| lauric acid | 2.1076 |
| fragrance | 1.5000 |
| polyethylene glycol (PEG-8) | 1.4994 |
| chelating agent (pentasodium pentetate) | 0.2108 |
| chelating agent (tetrasodium etidronate) | 0.2108 |
| antibacterial agent (triclosan) | 0.1999 |
| sodium chloride | 0.1341 |
| vitamin additives | 0.1000 |
| citric acid | 0.0479 |

-continued

| Component | wt. % |
|---|---|
| dye (red 4) | 0.0003 |
| dye (yellow 5) | 0.0003 |
| Total | 100.00 |

While the above example illustrates a soap composition comprising a soap mixture of sodium tallowate, sodium palm kernelate, sodium palmitate and sodium stearate, free fatty acid of lauric acid, and a polyalkylene glycol of PEG-8, it will be appreciated that any other suitable soap mixture, free fatty acid and polyalkylene glycol may be used and may be present in any suitable amount. It will further be appreciated that although an example of a soap composition comprising glycerin is illustrated above, sorbitol or a sorbitol and glycerin mixture could also be used. Similarly, while the above example illustrates use of chelating agents, dyes, fragrance, bacterial agent and vitamins, it will be understood that any other conventional, suitable additive or combination of additives, present in any suitable proportion, may be used. Further, it will be appreciated that any such additives may be absent from the translucent soap bar composition altogether.

To evidence the performance characteristics of various formulations of the translucent soap bar compositions according to the present invention, tests were conducted to determine the difference in translucency between soap compositions with a polyalkylene glycol and those without. Ten peach-colored translucent soap bars, Sample A, were manufactured using the formulation and process described above, each soap bar comprising about 1.5% PEG-8. Ten other peach-colored translucent soap bars, Sample B, were manufactured using the same formulation and process as those of the soap bars of Sample A, except the soap bars of Sample B did not contain any polyalkylene glycol.

Similarly, ten teal-colored translucent soap bars, Sample C, were manufactured using a formulation and process similar to those described above, each soap bar comprising about 1.5% PEG-8, although variations in dye color to accommodate teal-colored bars were implemented. Ten other teal-colored translucent soap bars, Sample D, were manufactured using the same formulation and process as those of the soap bars of Sample C, except that the soap bars of Sample D did not contain any polyalkylene glycol.

Opacity measurements were taken on a Hunter Lab Color Quest II colorimeter capable of measuring the reflectance of light through a sample bar, first against a white background and then against a black background. Opacity of the soap bars was calculated according to the equation:

$$\%\ \text{Opacity} = \left[\frac{Y_{black\_background}}{Y_{white\_background}}\right] \times 100$$

where $Y_{black\_background}$ is the reflectance value of a soap bar against a black background and $Y_{white\_background}$ is the reflectance value of the soap bar against a white background. As reflectance increases (i.e., as translucency improves), $Y_{white\_background}$ increases and $Y_{black\_background}$ decreases. Thus, as opacity decreases, translucency increases.

Table 1 illustrates the increase in translucency between Sample A, the peach-colored soap bars without PEG-8, and Sample B, the peach-colored soap bars with PEG-8:

TABLE 1

| Sample A (Peach) | Opacity | Sample B (Peach) | Opacity | % Increase Translucency |
|---|---|---|---|---|
| Bar 1 | 94.09 | Bar 1 | 79.04 | 16.00 |
| Bar 2 | 93.18 | Bar 2 | 78.16 | 16.12 |
| Bar 3 | 94.85 | Bar 3 | 78.43 | 17.31 |
| Bar 4 | 94.45 | Bar 4 | 79.68 | 15.64 |
| Bar 5 | 94.82 | Bar 5 | 82.53 | 12.96 |
| Bar 6 | 95.87 | Bar 6 | 79.00 | 17.60 |
| Bar 7 | 93.52 | Bar 7 | 81.70 | 12.64 |
| Bar 8 | 95.15 | Bar 8 | 77.72 | 18.32 |
| Bar 9 | 95.15 | Bar 9 | 78.45 | 17.55 |
| Bar 10 | 93.77 | Bar 10 | 77.83 | 17.00 |
| | | | Overall Average: | 16.11% |

Similarly, Table 2 illustrates the increase in translucency between Sample C, the teal-colored soap bars without PEG-8, and Sample D, the teal-colored soap bars with PEG-8:

TABLE 2

| Sample C (Teal) | Opacity | Sample D (Teal) | Opacity | % Increase Translucency |
|---|---|---|---|---|
| Bar 1 | 97.12 | Bar 1 | 84.12 | 13.39 |
| Bar 2 | 96.69 | Bar 2 | 86.09 | 10.96 |
| Bar 3 | 96.49 | Bar 3 | 84.97 | 11.94 |
| Bar 4 | 97.26 | Bar 4 | 83.43 | 14.22 |
| Bar 5 | 96.91 | Bar 5 | 87.57 | 9.64 |
| Bar 6 | 97.28 | Bar 6 | 86.05 | 11.54 |
| Bar 7 | 96.66 | Bar 7 | 83.14 | 13.99 |
| Bar 8 | 96.57 | Bar 8 | 86.43 | 10.50 |
| Bar 9 | 97.60 | Bar 9 | 86.34 | 11.54 |
| Bar 10 | 96.69 | Bar 10 | 84.88 | 12.21 |
| | | | Overall Average: | 11.99% |

The above results illustrate that the addition of a polyalkylene glycol in an amount as small as 1.5% by weight of the soap composition increased the translucency of the soap bar composition to an extent noticeable to a consumer. For the peach-colored soap bars, translucency increased an average of about 16.11%. For the teal-colored soap bars, translucency increased an average of about 12%.

As should now be appreciated, the translucent soap bar composition, in accordance with the various embodiments of the present invention evidences translucent properties while comprising a soap mixture, glycerin, water and a relatively small amount of a polyalkylene glycol having a low molecular weight. It will be appreciated in accordance with principles of the present invention, various other additives can be used without significantly affecting the translucent properties of the soap composition.

In the foregoing specification, the invention has been described with reference to specific embodiments. However, one of ordinary skill in the art appreciates that various modifications and changes can be made without departing from the scope of the present invention as set forth in the claims below. Accordingly, the specification is to be regarded in an illustrative rather than a restrictive sense, and all such modifications are intended to be included within the scope of the present invention.

Benefits, other advantages, and solutions to the problems have been described above with regard to specific embodi ments. However, the benefits, advantages, solutions to problems, and any element(s) that may cause any benefit, advantage, or solution to occur or become more pronounced are not to be construed as a critical, required, or essential feature or element of any or all the claims. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

We claim:

1. A translucent soap bar comprising, by weight:

about 65 to about 80% of a soap mixture;

about 0.5 to about 5.0% of a polyethylene glycol having a molecular weight in the range of about 300 to about 800;

about 4.5 to about 8.5% glycerin;

about 12 to about 16% water, and optionally, about 1.5 to about 3.0% of a free fatty acid.

2. The translucent soap bar of claim 1, said soap mixture comprising at least one of sodium tallowate, sodium palmitate, sodium stearate and sodium palm kernelate.

3. The translucent soap bar of claim 1, the translucent soap bar comprising about 70 to about 75% soap mixture.

4. The translucent soap bar of claim 1, the translucent soap bar comprising about 6.0 to about 8.0% glycerin.

5. The translucent soap bar of claim 1, said polyethylene glycol comprising PEG-8.

6. The translucent soap bar of claim 1, the translucent soap bar comprising about 1.0 to about 2.0% polyethylene glycol.

7. The translucent soap bar of claim 1, said free fatty acid having an alkyl chain length with 8 to 22 carbon atoms.

8. The translucent soap bar of claim 7, said free fatty acid comprising lauric acid.

* * * * *